(12) United States Patent
Elborno (10) Patent No.: US 9,561,371 B2
(45) Date of Patent: Feb. 7, 2017

(54) SYSTEMS AND METHODS FOR TREATING ESSENTIAL TREMOR OR RESTLESS LEG SYNDROME USING SPINAL CORD STIMULATION

(71) Applicant: BOSTON SCIENTIFIC NEUROMODULATION CORPORATION, Valencia, CA (US)

(72) Inventor: Ahmed A. Elborno, Oak Brook, IL (US)

( * ) Notice: Subject to any disclaimer, the term of this patent is extended or adjusted under 35 U.S.C. 154(b) by 0 days.

(21) Appl. No.: 14/531,818

(22) Filed: Nov. 3, 2014

(65) Prior Publication Data
US 2015/0066105 A1  Mar. 5, 2015

Related U.S. Application Data

(63) Continuation of application No. 12/258,317, filed on Oct. 24, 2008, now abandoned, which is a continuation-in-part of application No. 12/180,924, filed on Jul. 28, 2008, now abandoned.

(51) Int. Cl.
*A61N 1/36* (2006.01)
*A61N 1/05* (2006.01)
*A61N 1/375* (2006.01)

(52) U.S. Cl.
CPC ......... *A61N 1/36067* (2013.01); *A61N 1/0553* (2013.01); *A61N 1/0556* (2013.01); *A61N 1/36071* (2013.01); *A61N 1/36082* (2013.01); *A61N 1/3752* (2013.01)

(58) Field of Classification Search
CPC .............. A61N 1/0553; A61N 1/36067; A61N 1/36082
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |

(Continued)

OTHER PUBLICATIONS

Official Communication for U.S. Appl. No. 12/180,924 mailed Sep. 28, 2010.

(Continued)

*Primary Examiner* — Joseph Dietrich
(74) *Attorney, Agent, or Firm* — Lowe Graham Jones PLLC; Bruce E. Black (57) ABSTRACT

A method for treating essential tremor or restless leg syndrome using spinal cord stimulation includes implanting a lead near a spinal cord of a patient. The lead includes a plurality of electrodes disposed on a distal end of the lead and electrically coupled to at least one contact terminal disposed on a proximal end of the lead. Electrical signals are provided from a control module coupled to the lead to stimulate a portion of the spinal cord of the patient using at least one of the electrodes. The electrical signals reduce, alleviate, or eliminate at least one adverse effect of essential tremor or restless leg syndrome.

14 Claims, 8 Drawing Sheets

(56) References Cited

U.S. PATENT DOCUMENTS

| | | |
|---|---|---|
| 8,175,710 B2 | 5/2012 | He |
| 8,224,450 B2 | 7/2012 | Brase |
| 8,364,278 B2 | 1/2013 | Pianca et al. |
| 8,700,178 B2 | 4/2014 | Anderson |
| 2004/0059392 A1 | 3/2004 | Parramon et al. |
| 2004/0098074 A1* | 5/2004 | Erickson .............. A61N 1/0534 607/117 |
| 2006/0052856 A1 | 3/2006 | Kim et al. |
| 2007/0060954 A1 | 3/2007 | Cameron et al. |

OTHER PUBLICATIONS

Official Communication for U.S. Appl. No. 12/180,924 mailed May 11, 2011.
Official Communication for U.S. Appl. No. 12/258,317 mailed Sep. 28, 2010.
Official Communication for U.S. Appl. No. 12/258,317 mailed May 31, 2011.
J K Krauss, et al. Chronic Spinal Cord Stimulation in Medically Intractable Orthostatic Tremor, J Neurol Neurosurg Psychiatry, 2006, p. 1013-1016, 77.
Deuschl, et al. "The Pathophysiology of Parkinsonian Tremor: A review." Journal of Neurology (2000) 247 [Suppl 5]: V/33-V/48. (16 pages).

\* cited by examiner

SYSTEMS AND METHODS FOR TREATING ESSENTIAL TREMOR OR RESTLESS LEG SYNDROME USING SPINAL CORD STIMULATION

CROSS-REFERENCE TO RELATED APPLICATIONS

This application is a continuation of U.S. Ser. No. 12/258,317 filed Oct. 24, 2008 which is a continuation-in-part of U.S. Ser. No. 12/180,924, filed Jul. 28, 2008, the benefit of the earlier filing date of which is hereby claimed under 35 U.S.C. §120, and the entire contents of which are hereby incorporated by reference.

FIELD

The present invention is directed to the area of implantable spinal cord stimulation systems and methods of making and using the systems. The present invention is also directed to the use of implantable spinal cord stimulation systems for treating Parkinsonism, essential tremor, or restless leg syndrome, as well as methods of making the spinal cord stimulation systems.

BACKGROUND

Parkinsonism is a neurodegenerative syndrome of the central nervous system that belongs to a group of conditions called motor system disorders. The symptoms of Parkinsonism may vary from patient to patient. In general, Parkinsonism impairs motor skills and speech, as well as other functions. Most patients experience tremors (resting or functional) in one or more body locations (e.g., at least one hand or arm, foot or leg, jaw, face, and the like), rigidity (e.g., stiffness in one or more of the limbs or trunk), slowness of movement (bradykinesia), or postural instability (e.g., impaired balance or coordination, stooping posture, etc.). Many additional signs and symptoms may also occur including, for example, difficulty with speech and swallowing, difficulty with limb movement (e.g., shuffling gate), fatigue, reduced facial expressions (i.e., facial masking), mood disturbances, reduced sensation, reduced cognitive ability, incontinence, light sensitivity, and dermatitis.

There are many known underlying causes of Parkinsonism including, for example, Parkinson's disease, Autoimmune Deficiency Syndrome (AIDS), corticobasal degeneration, Creutzfeldt-Jakob disease, diffuse Lewy body disease, drug-induced Parkinsonism, encephalitis lethargica, multiple system atrophy, pantothenate kinase-associated neurodegeneration, progressive supranuclear palsy, exposure to toxins (e.g., carbon monoxide, carbon disulfide, manganese, paraquat, hexane, rotenone, toluene, and the like), side effects of medications (e.g., phenothiazines, thioxanthenes, butyrophenones, piperazines, antidepressants, and the like), vascular Parkinsonism, Wilson's disease, parancoplastic syndrome, head trauma, mental disorders, and the like.

Currently there is no known cure for Parkinsonism. Many patients suffering from Parkinsonism take one or more medications for reducing, alleviating, or eliminating one or more of the symptoms of Parkinsonism. However, some patients are either unresponsive to medications or detrimentally affected by medications and, instead, undergo brain surgery to reduce, alleviate, or eliminate one or more Parkinsonism-related symptoms.

Essential tremor is a progressive neurological disease. The symptoms of essential tremor may vary from patient to patient. Many patients experience tremors. Some patients may experience impaired speech in addition to, or instead of, tremors. Most patients experience tremors during voluntary movement which dissipate during sleep or periods of inactivity. Tremors may occur in the upper body, for example, in one or more of the arms and hands, as well as in the head, neck, jaw, eyelids, and voice. However, tremors may also occur in one or more of the lower extremities. Essential tremor patients may also experience one or more additional signs and symptoms including, for example, decreased balance, anxiety, depression, decreased cognitive ability, and dementia. Some patients may experience an increase in the severity of essential tremors in response to caffeine, tobacco, fatigue, fear, anger, low blood sugar, lithium salts, antidepressants, and the like.

Currently there is no known cure for essential tremor. Many patients suffering from one or more of the adverse affects of essential tremor take one or more medications for reducing, alleviating, or eliminating one or more of the symptoms of essential tremor. However, some patients are either unresponsive to medications or detrimentally affected by medications and, instead, undergo brain surgery to reduce, alleviate, or eliminate one or more of the symptoms of essential tremor.

Restless leg syndrome is a progressive disease of the nervous system often characterized by an irresistible urge to move one's body in response to an unpleasant sensation that is sometimes characterized as being uncomfortable, creepy, like pins-and-needles, itchy, tickly, or burning. Many patients may experience the unpleasant sensation in at least one lower leg. However, some patients with restless leg syndrome experience the unpleasant sensation in other body locations in addition to, or instead of, the legs including, for example, one or both feet, one or both thighs, the torso, or one or both arms. Some patients may experience an increase in the severity of the unpleasant sensation as the day progresses from morning to evening. Additionally, some patients may experience an increase in the severity of the unpleasant sensations when sitting or lying down. Some patients only experience the unpleasant sensations when sitting or lying down.

Patients with restless leg syndrome may also experience one or more additional signs and symptoms including, for example, walking discomfort, insomnia, sleepiness, anxiety, depression, confusion, and decreased cognitive ability. Some restless leg syndrome patients may experience an increase in the severity of restless leg syndrome in response to iron deficiency, stress, hypoglycemia, pregnancy, alcohol, caffeine, undergoing surgery, aberrant dopamine levels, varicose veins, folate deficiency, sleep apnea, uremia, diabetes, thyroid disease, peripheral neuropathy, anticonvulsive medication, lithium salts, tobacco, antidepressants, beta blockers, H2 blockers, antipsychotics, Lyme disease, magnesium deficiency, vitamin B-12 deficiency, amyloidosis, kidney disease, Parkinson's disease, and some autoimmune diseases such as Sjögren's syndrome, celiac disease, and rheumatoid arthritis.

Currently there is no known cure for restless leg syndrome. Some patients with restless leg syndrome take one or more medications or vitamin or mineral supplements for reducing, alleviating, or eliminating one or more of the symptoms of restless leg syndrome. However, some patients are either unresponsive to, or detrimentally affected by, medications or vitamin or mineral supplements.

BRIEF SUMMARY

In one embodiment, a method for treating essential tremor using spinal cord stimulation includes implanting a lead near a spinal cord of a patient. The lead includes a plurality of electrodes disposed on a distal end of the lead and electrically coupled to at least one contact terminal disposed on a proximal end of the lead. Electrical signals are provided from a control module coupled to the lead to stimulate a portion of the spinal cord of the patient using at least one of the electrodes. The electrical signals reduce, alleviate, or eliminate at least one adverse effect of essential tremor.

In another embodiment, an implantable system for treating essential tremor includes a lead and a control module. The lead has a distal end and a proximal end and is configured and arranged for implantation near a spinal cord of a patient. The lead includes a plurality of electrodes disposed on the distal end, a plurality of terminals disposed on the proximal end, and a plurality of conductors that each electrically couple at least one of the electrodes to at least one of the terminal. The control module is configured and arranged to electrically couple to the lead. The control module includes a housing and an electronic subassembly disposed in the housing.

In yet another embodiment, a method for treating restless leg syndrome using spinal cord stimulation includes implanting a lead near a spinal cord of a patient. The lead includes a plurality of electrodes disposed on a distal end of the lead and electrically coupled to at least one contact terminal disposed on a proximal end of the lead. Electrical signals are provided from a control module coupled to the lead to stimulate a portion of the spinal cord of the patient using at least one of the electrodes. The electrical signals reduce, alleviate, or eliminate at least one adverse effect of restless leg syndrome.

In still yet another embodiment, an implantable system for treating restless leg syndrome includes a lead and a control module. The lead has a distal end and a proximal end and is configured and arranged for implantation near a spinal cord of a patient. The lead includes a plurality of electrodes disposed on the distal end, a plurality of terminals disposed on the proximal end, and a plurality of conductors that each electrically couple at least one of the electrodes to at least one of the terminal. The control module is configured and arranged to electrically couple to the lead. The control module includes a housing and an electronic subassembly disposed in the housing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified. For a better understanding of the present invention, reference will be made to the following Detailed Description, which is to be read in association with the accompanying drawings, wherein.

DETAILED DESCRIPTION

The present invention is directed to the area of implantable spinal cord stimulation systems and methods of making and using the systems. The present invention is also directed to the use of implantable spinal cord stimulation systems for treating Parkinsonism, essential tremors, or restless leg syndrome, as well as methods of making the spinal cord stimulation systems.

Spinal cord stimulation involves delivering an electrical current to a site on or near a target nerve. This stimulation generally creates a tingling sensation, known as parasthesia, throughout a particular region of the body associated with the stimulated nerve. The size, intensity, and character of the parasthesia may be controlled by adjusting the parameters (e.g., stimulus pulsewidth, amplitude, and frequency) of the stimulating current.

It has been discovered that stimulating the spinal cord with an electrical stimulation current in proximity to selected nerves can alleviate or eliminate one or more of the adverse effects of Parkinsonism occurring at the site of skeletal muscle to which the one or more stimulated nerves couple. Thus, abnormalities that originate from the brain due to Parkinsonism can be modulated at the level of the spinal cord to normalize movement adversely affected by the Parkinsonism.

Dopamine is a neurotransmitter involved in the control of body movement. Although the present invention is not limited by any particular theory, it is thought that the symptoms of Parkinsonism arise when dopamine-secreting cells degenerate, causing a subsequent depletion of dopamine in other portions of the brain. Eventually, deficient dopamine levels results in undesired signals being sent to skeletal muscles, thereby causing disordered body movements. It is thought that, stimulating the spinal cord in proximity to one or more nerves transmitting the undesired signals to skeletal muscles can be used to counteract the ill effects of deficient dopamine levels and normalize muscle movement.

Figure 1:
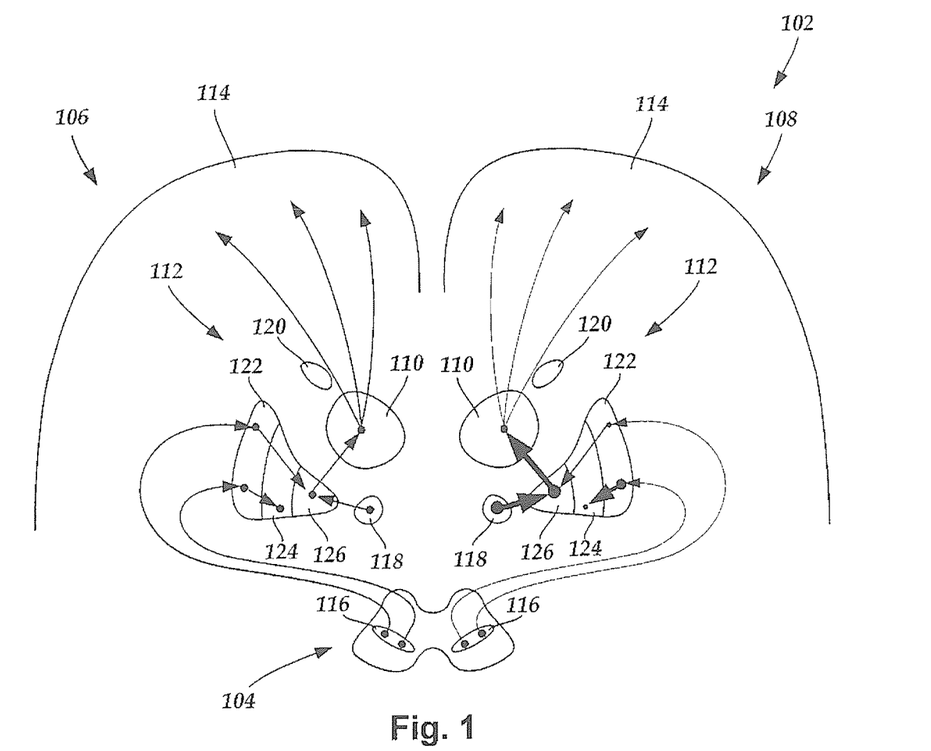
FIG. 1 is a schematic view of one embodiment of dopaminergic pathways in a brain, the left side of the brain showing a normal dopaminergic pathway and the right side of the brain showing an abnormal dopaminergic pathway for a patient with Parkinson's disease, according to the invention.

FIG. 1 is a schematic view of one embodiment of dopaminergic pathways in a brain 102 under normal conditions (left side) and with Parkinson's disease (right side). The brain 102 includes a midbrain (mesencephalon) 104, a left hemisphere 106, and a right hemisphere 108. Each of the hemispheres 106 and 108 include a thalamus 110, a basal ganglia 112, and a cerebral cortex 114. Each of the basal ganglia 112 includes a substantia nigra 116, a subthalamic nucleus 118, a caudate nucleus 120, a putamcen 122, a globus pallidus externus 124, and a globus pallidus internus 126.

Dopamine is secreted from dopaminergic cells in the substantia nigra 116 and transported to other portions of the basal ganglia 122 before transport to the thalamus 110 and the cerebral cortex 114. Each of the other portions of the brain 102 through which dopamine interacts is involved in the control of movement. By interacting with these other regions, the substantia nigra 116 facilitates smooth, fluid, and controlled movement. The left hemisphere 106 includes arrows of uniform thickness showing an exemplary normal amount of dopamine along a dopaminergic pathway. The right hemisphere 108 includes arrows of various thicknesses showing an exemplary abnormal dopaminergic pathway consistent with a patient with Parkinsonism. As dopamine-secreting cells degenerate, reduced amounts of dopamine are released, resulting in reduced stimulation of dopamine-receiving cells, which, in turn, results in many different possible adverse affects, such as disordered movement.

One of the hallmarks of Parkinsonism is tremors, either resting or functional. The mechanisms of Parkinsonian tremor are currently not fully understood. Although the present invention is not limited by any particular theory, at least some theories suggest that Parkinsonian tremor is due to oscillating neuronal activity within the central nervous system. At least some studies have shown that multiple oscillators are involved which are believed to be produced in basal ganglia loops.

The neuronal mechanisms forming the oscillations are also currently not fully understood. Several possible hypotheses for neuronal mechanisms forming the oscillations have been proposed based on animal models and collected patient data. One hypothesis suggests that oscillations form from hyperpolarization of cells within a cortico-subthalamo-pallido-thalamic loop. Another hypothesis suggests that hyperpolarization of cells form a pacemaker in the globus pallidus externus 124 and the subthalamic nucleus 118. Yet another hypothesis suggests that abnormal synchronization is due to unknown mechanisms within a striato-pallido-thalamic pathway which leads to a loss of segregation between two or more of the basal ganglia loops.

Currently, Parkinsonism is managed in many patients by medication or brain surgery. Two common types of medications are levodopa and dopamine agonists. Levodopa transforms into dopamine in the brain and can be used to supplement reduced dopamine levels. Unfortunately, because levodopa is also metabolized in other regions of a patient's body, many possible side effects may result from continued use of levodopa including, for example, nausea, vomiting, orthostatic hypotension, excessive sleepiness, hallucinations, dyskinesias, and the like or combinations thereof. Additionally, due to feedback inhibition, increased circulation of levodopa may result in reduced endogenous levodopa formation.

Dopamine agonists (e.g., pergolide, pramipexole, bromocriptine, ropinirole, and apo-morphine) are medications that mimic the effect of dopamine on the cells which normally receive dopamine from the substantia nigra 116. Unfortunately, long-term use of dopamine agonists may result in similar side effects as with levodopa. Other medications may be used in conjunction with levodopa or dopamine agonists, or in lieu of levodopa or dopamine agonists including, for example, carbidopa, catechol-O-methyl transferase (COMT) inhibitors, anti-cholinergics, selegiline, amantadine, and the like or combinations thereof.

Brain surgery is a treatment option for patients with late-stage Parkinsonism or patients that are unresponsive to medications or that exhibit unacceptable levels of dyskinesias, or other adverse effects, at therapeutic levels of medication. It is possible that brain surgery disrupts oscillations by desynchronizing the activity of one or more of the pathways discussed above. Two common types of brain surgery include ablation and deep brain stimulation. Ablative surgery removes or destroys a malfunctioning portion of the brain in order to restore balance of neural activity with the movement control centers of the brain. Ablation may be performed at one or more of the movement control centers of the brain including, for example, the globus pallidus internus (a "pallidotomy"), or the thalamus. However, ablation can be difficult, dangerous, invasive, and expensive.

Deep brain stimulation provides high-frequency electrical stimulation to a region surrounding an abnormally functioning structure, such as the globus pallidus internus 126 or the subthalamic nucleus 118. The stimulation causes global hyperpolarization of cell membranes which, in turn, causes a reduction of excitability and subsequent tremor. In other words, the stimulation jams signal flow out of the abnormally functioning structure, thereby disrupting abnormal oscillations. Additionally, antidromic or orthodromic depolarization currents may form which may modulate neural activity at remote locations.

Figure 2:
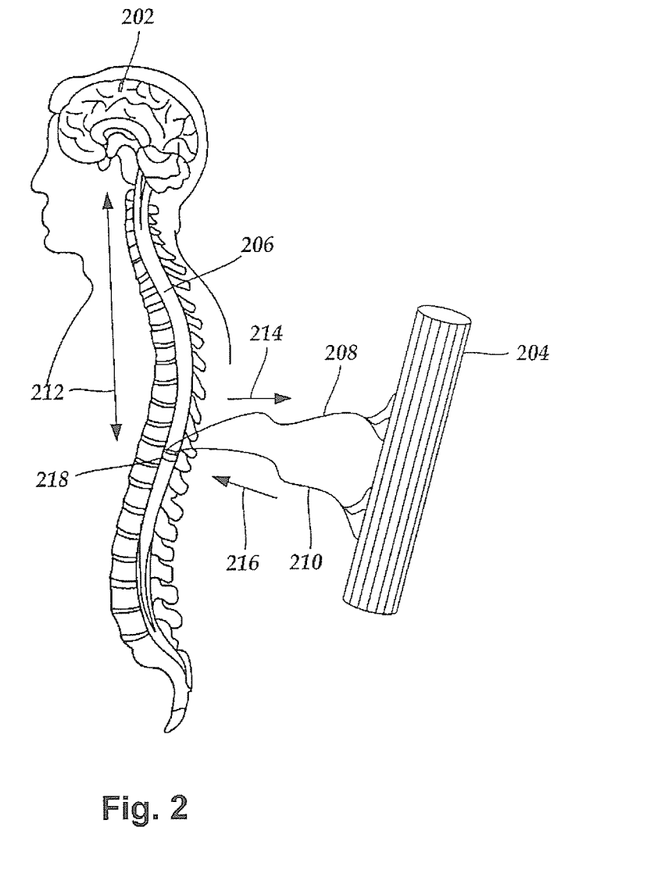
FIG. 2 is a schematic view of one embodiment of a brain coupled to a skeletal muscle via a spinal cord, motor nerves, and sensory nerves, according to the invention.

As discussed above, abnormal levels of dopamine may eventually lead to disordered movements. Dopamine-initiated signals originating in the brain are transmitted to skeletal muscles via the peripheral nervous system. FIG. 2 is a schematic view of one embodiment of a brain 202 coupled to a skeletal muscle 204 via a spinal cord 206, motor nerves 208, and sensory nerves 210. Typically, signals transmit in both directions along a longitudinal length of the spinal cord 206, as shown by two-headed directional arrow 212, and in only one direction along a longitudinal length of the motor nerves 208 and a longitudinal length of the sensory nerves 210, as shown by directional arrows 214 and 216, respectively.

The motor nerves 208 and the sensory nerves 210 that couple with the muscle 204 at one end, couple to the spinal cord 206 at a segment 218 which contains the roots of the motor nerves 208 and the sensory nerves 210. Other skeletal muscles in different locations in a patient attach at different segments along the longitudinal length of the spinal cord 206.

Figure 3:
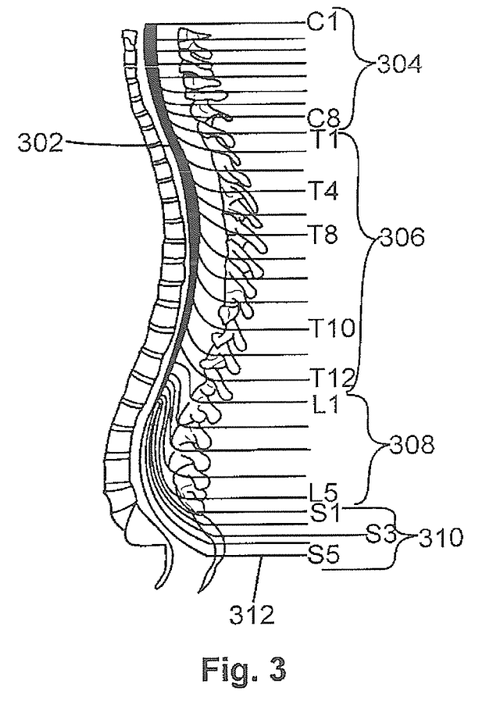
FIG. 3 is a schematic side view of one embodiment of a spinal cord, according to the invention.

FIG. 3 is a schematic side view of one embodiment of a spinal cord 302. The spinal cord 302 is typically divided into thirty-one different segments which connect to the spinal cord 302 between vertebrae of a vertebral column. Each segment includes motor and sensory nerve roots. There are typically eight cervical segments (C1-C8) 304, twelve thoracic segments (T1-T12) 306, five lumbar segments (L1-L5) 308, five sacral segments (S1-S5) 310, and a coccygeal segment 312.

Each segment of the spinal cord 302 sends and receives signals corresponding to muscle movement, such as skeletal muscle movement at different locations of a patient's body. For example, muscles used to control movement of the head and neck typically connect to the spinal cord 302 at C1-C3; muscles used to control movement of the hands typically connect to the spinal cord 302 at T1; muscles used to control movement of the wrists and elbows typically connect to the spinal cord 302 at C6-C7; muscles used to control movement of the hips typically connect to the spinal cord 302 at L2; muscles used to control movement of the quadriceps typically connect to the spinal cord 302 at L3; muscles used to control movement of the hamstrings and knees typically connect to the spinal cord 302 at L4-L5; and muscles used to control movement of the feet and knees typically connect to the spinal cord 302 at L4-S1.

In at least some embodiments, Parkinsonism may be treated using spinal cord stimulation. Although the present invention is not limited by any particular theory, at least one patient has shown that the symptoms of Parkinsonism can be reduced, alleviated, and even eliminated, by stimulating the spinal cord at the segment of the spinal cord connecting motor and sensory nerves to skeletal muscles affected by Parkinsonism. For example, for a patient with a hand tremor, the hand tremor may be alleviated, or even entirely eliminated, by implanting a spinal cord stimulation lead ("lead") adjacent to the patient's spinal cord at T1. As discussed below, in at least some embodiments, tremors that are unrelated to Parkinsonism may also be treated using spinal cold stimulation.

In at least some embodiments, a lead is positioned in proximity to one or more motor nerves. When a motor nerve is stimulated, the motor nerve transmits electrical pulses along the motor nerve to one or more attached muscle fibers and elicits contractions in the attached muscle fiber(s). In at least some embodiments, a lead is positioned in proximity to one or more sensory nerves. When a sensory nerve is stimulated, the sensory nerve produces an electrical impulse that is transmitted along the nerve into the spinal cord, where it can produce perceptible sensations, modulation of spinal cord circuits, and reflex effects on motor pathways. In at least some embodiments, a lead is positioned in proximity to one or more motor nerves and one or more sensory nerves. In at least some embodiments, a plurality of leads may be used to stimulate one or more motor or sensory nerves coupled to one or more muscles or muscle groups.

In at least some embodiments, Parkinsonism-related tremors of at least a portion of one of the upper extremities are reduced, alleviated, or eliminated by spinal cord stimulation. In at least some embodiments, Parkinsonism-related tremors of at least a portion of one of the lower extremities are reduced, alleviated, or eliminated by spinal cord stimulation. In at least some embodiments, Parkinsonism-related tremors of at least a portion of one of the upper extremities and at least a portion of one of the lower extremities are reduced, alleviated, or eliminated by spinal cord stimulation.

In at least some embodiments, Parkinsonism-related tremors are reduced, alleviated, or eliminated in severity by spinal cord stimulation. In at least some embodiments, Parkinsonism-related tremors are reduced, alleviated, or eliminated in frequency by spinal cord stimulation. In at least some embodiments, Parkinsonism-related tremors are reduced, alleviated, or eliminated in severity and in frequency by spinal cord stimulation.

In at least some embodiments, Parkinsonism-related functional tremors are reduced, alleviated, or eliminated by spinal cord stimulation. In at least some embodiments, Parkinsonism-related resting tremors are reduced, alleviated, or eliminated by spinal cord stimulation. In at least some embodiments, both Parkinsonism-related functional tremors and resting tremors are reduced, alleviated, or eliminated by spinal cord stimulation.

In at least some embodiments, tremors (either resting or functional) are reduced, alleviated, or eliminated in severity by spinal cord stimulation. In at least some embodiments, tremors (either resting or functional) are reduced, alleviated, or eliminated in frequency by spinal cord stimulation. In at least some embodiments, tremors (either resting or functional) are reduced, alleviated, or eliminated in severity and in frequency by spinal cord stimulation.

In at least some embodiments, Parkinsonism-related bradykinesia is reduced, alleviated, or eliminated in a patient by spinal cord stimulation. In at least some embodiments, Parkinsonism-related shuffling gate is reduced, alleviated, or eliminated in a patient by spinal cord stimulation. In at least some embodiments, Parkinsonism-related stooping posture is reduced, alleviated, or eliminated in a patient by spinal cord stimulation. In at least some embodiments, Parkinsonism-related pain associated with one or more body regions is reduced, alleviated, or eliminated in a patient by spinal cord stimulation.

In one patient, the spinal cord of a patient with Parkinsonism was stimulated and the results were monitored over a five month period. At the beginning of the study, the patient presented with resting and functional tremors of the upper and lower extremities, pain in the upper and lower extremities, bradykinesia in the upper extremities, as well as a shuffling gait. Due to instability, the patient had been confined to a motorized wheelchair for twelve years which the patient had difficulty operating due to the severity of the right upper-extremity tremors. After a five day trial period for the lower extremities, the patient was able to stand up and walk approximately 70 feet without assistance. The patient was subsequently fitted with a permanent stimulator. After three weeks, the associated pain was reduced 80-90%, the shuffling gait was eliminated, the instability was eliminated, the patient was able to walk, and the tremors were eliminated in the lower extremities. A trial stimulation was subsequently performed on the upper extremities two-months later. After the 5 day trial period for the upper extremities, the tremors were eliminated, the associated pain was eliminated, and the bradykinesia was eliminated. Additionally, the patient showed reduced light sensitivity and showed improved mental focus. Moreover, the patient showed increased ability to form facial expressions.

In at least some embodiments, stimulating the spinal cord with an electrical stimulation current in proximity to selected nerves can reduce, alleviate, or eliminate one or more of the adverse effects of essential tremor occurring at the site of skeletal muscle to which the one or more stimulated nerves couple. Thus, abnormalities that originate from the brain due to essential tremor can be modulated at the level of the spinal cord to normalize movement adversely affected by the essential tremor.

The mechanisms of essential tremor are currently not fully understood. Although the present invention is not limited by any particular theory, at least some theories suggest that essential tremor is due to disorders of the cerebellum or the cerebello-thalamo-cortical circuits or an abnormally functioning central oscillator.

Currently, essential tremor is managed in many patients by medication or brain surgery. Common types of medications are tranquilizers (e.g., alprazolam, clonazepam, or diazepam), beta-blockers (e.g., propranolol, atenolol, metoprolol, or nadolol), antiseizure medications (e.g., primidone, gabapentin, or topiramate), antipsychotics (e.g., clozapine), antidepressants (e.g., mirtazapine), and calcium-channel blockers (e.g., flunarizine or nimodipine), as well as alcohol and botulinum toxin. Many different adverse side effects may result from continued use of beta-blockers or antiseizure medication including, for example, fatigue, shortness of breath, decreased heart rate, nasal congestion, drowsiness, difficulty concentrating, nausea, decreased coordination, and the like or combinations thereof.

Brain surgery is a treatment option for patients with severe essential tremor or patients that are unresponsive to medications or that exhibit unacceptable levels of dyskinesias, or other adverse effects, at therapeutic levels of medication. It is possible that brain surgery disrupts oscillations by desynchronizing the activity of one or more of the pathways discussed above. Two common types of brain surgery include ablation and deep brain stimulation. Ablative surgery removes or destroys a malfunctioning portion of the brain in order to restore balance of neural activity with the movement control centers of the brain. Ablation may be performed at one or more of the movement control centers of the brain including, for example, the thalamus. However, ablation can be difficult, dangerous, invasive, and expensive.

Deep brain stimulation provides high-frequency electrical stimulation to a region surrounding an abnormally functioning structure, such as the thalamus. The stimulation causes global hyperpolarization of cell membranes which, in turn, causes a reduction of excitability and subsequent tremor. In other words, the stimulation obstructs signal flow out of the abnormally functioning structure, thereby disrupting abnormal oscillations. Additionally, antidromic or orthodromic depolarization currents may form which may modulate neural activity at remote locations.

In at least some embodiments, essential tremor may be treated using spinal cord stimulation. Although the present invention is not limited by any particular theory, it has shown that the symptoms of essential tremor can be reduced, alleviated, and even eliminated, by stimulating the spinal cord at the segment of the spinal cord connecting motor or sensory nerves to skeletal muscles affected by essential tremor. For example, for a patient with a hand tremor, the hand tremor may be alleviated, or even entirely eliminated, by implanting a spinal cord stimulation lead ("lead") adjacent to the patient's spinal cord at T1.

In at least some embodiments, a lead is positioned in proximity to one or more motor nerves coupling the spinal cord to one or more skeletal muscles in the portion of the body affected by essential tremor. When a motor nerve is stimulated, the motor nerve transmits electrical pulses along the motor nerve to one or more attached muscle fibers and elicits contractions in the attached muscle fiber(s). In at least some embodiments, a lead is positioned in proximity to one or more sensory nerves coupling the spinal cord to one or more skeletal muscles in the portion of the body affected by essential tremor. When a sensory nerve is stimulated, the sensory nerve produces an electrical impulse that is transmitted along the nerve into the spinal cord, where it can produce perceptible sensations, modulation of spinal cord circuits, and reflex effects on motor pathways. In at least some embodiments, a lead is positioned in proximity to one or more motor nerves and one or more sensory nerves coupling the spinal cord to one or more skeletal muscles in the portion of the body affected by essential tremor. In at least some embodiments, a plurality of leads may be used to stimulate one or more motor or sensory nerves coupling one or more skeletal muscles in the spinal cord to the portion of the body affected by essential tremor.

In at least some embodiments, essential-tremor-related tremors of at least a portion of one of the upper extremities are reduced, alleviated, or eliminated by spinal cord stimulation. In at least some embodiments, essential-tremor-related tremors of at least a portion of one of the lower extremities are reduced, alleviated, or eliminated by spinal cord stimulation. In at least some embodiments, essential-tremor-related tremors of at least a portion of one of the upper extremities and at least a portion of one of the lower extremities are reduced, alleviated, or eliminated by spinal cord stimulation.

In at least some embodiments, essential-tremor-related tremors are reduced, alleviated, or eliminated in severity by spinal cord stimulation. In at least some embodiments, essential-tremor-related tremors are reduced, alleviated, or eliminated in frequency by spinal cord stimulation. In at least some embodiments, essential-tremor-related tremors are reduced, alleviated, or eliminated in severity and in frequency by spinal cord stimulation.

In at least some embodiments, stimulating the spinal cord with an electrical stimulation current in proximity to selected nerves can reduce, alleviate, or eliminate one or more of the adverse effects of restless leg syndrome occurring at the site of skeletal muscle to which the one or more stimulated nerves couple. Thus, abnormalities that originate from the brain due to restless leg syndrome can be modulated at the level of the spinal cord to normalize adversely affects caused by the restless leg syndrome.

Symptoms associated with restless leg syndrome may include an unpleasant sensation which may cause bodily movements to be made to temporarily reduce, alleviate, or eliminate the unpleasant sensation. As discussed above, the unpleasant sensation may occur at other body locations besides the leg including, for example, in the feet, hands, torso, or arms. The mechanisms of restless leg syndrome are currently not fully understood. Although the present invention is not limited by any particular theory, at least some theories suggest that restless leg syndrome is due to a dopamine imbalance.

Currently, restless leg syndrome is managed in many patients by medication. Common types of medications are pain relievers (e.g., ibuprofen, aspirin, or acetaminophen), medications taken for Parkinsonism (see above), opioids (e.g., codeine, oxycodone, methadone, or propoxyphene), muscle relaxants/sedatives (e.g., benzodiazepine, clonazepam, eszopiclone, ramelteon, temazepam, zaleplon, alprazolam, or zolpidem), antiseizure medications (e.g., gabapentin), tranquilizers (e.g., clonazepam), α2 adrenergic agonists (e.g., clonidine), and the like or combinations thereof.

In at least some embodiments, restless leg syndrome may be treated using spinal cord stimulation. Although the present invention is not limited by any particular theory, it has been shown that the symptoms of restless leg syndrome can be reduced, alleviated, and even eliminated, by stimulating the spinal cord at the segment of the spinal cord connecting motor and sensory nerves to skeletal muscles affected by restless leg syndrome. For example, for a patient with an unpleasant sensation in the foot, the unpleasant sensation may be alleviated, or even entirely eliminated, by implanting a spinal cord stimulation lead ("lead") adjacent to the patient's spinal cord at L4-S1.

In at least some embodiments, a lead is positioned in proximity to one or more motor nerves coupling the spinal cord to one or more skeletal muscles in the portion of the body affected by restless leg syndrome. When a motor nerve is stimulated, the motor nerve transmits electrical pulses along the motor nerve to one or more attached muscle fibers and elicits contractions in the attached muscle fiber(s). In at least some embodiments, a lead is positioned in proximity to one or more sensory nerves coupling the spinal cord to one or more skeletal muscles in the portion of the body affected by restless leg syndrome. When a sensory nerve is stimulated, the sensory nerve produces an electrical impulse that is transmitted along the nerve into the spinal cord, where it can produce perceptible sensations, modulation of spinal cord circuits, and reflex effects on motor pathways. In at least some embodiments, a lead is positioned in proximity to one or more motor nerves and one or more sensory nerves coupling the spinal cord to one or more skeletal muscles in the portion of the body affected by restless leg syndrome. In at least some embodiments, a plurality of leads may be used to stimulate one or more motor or sensory nerves coupling the spinal cord to one or more skeletal muscles in the portion of the body affected by restless leg syndrome.

In at least some embodiments, restless-leg-syndrome-related unpleasant sensations of at least a portion of one of the upper extremities are reduced, alleviated, or eliminated by spinal cord stimulation. In at least some embodiments, restless-leg-syndrome-related unpleasant sensations of at least a portion of one of the lower extremities are reduced, alleviated, or eliminated by spinal cord stimulation. In at least some embodiments, restless-leg-syndrome-related unpleasant sensations of at least a portion of one of the upper extremities and at least a portion of one of the lower extremities are reduced, alleviated, or eliminated by spinal cord stimulation.

In at least some embodiments, restless-leg-syndrome-related unpleasant sensations are reduced, alleviated, or eliminated in severity by spinal cord stimulation. In at least some embodiments, restless-leg-syndrome-related unpleasant sensations are reduced, alleviated, or eliminated in frequency by spinal cord stimulation. In at least some embodiments, restless-leg-syndrome-related unpleasant sensations are reduced, alleviated, or eliminated in severity and in frequency by spinal cord stimulation.

Suitable implantable spinal cord stimulation systems include, but are not limited to, a spinal cord stimulation lead ("lead") with one or more electrodes disposed on a distal end of the lead and one or more terminals disposed on one or more proximal ends of the lead. Leads include, for example, percutaneous leads, paddle leads, and cuff leads. Examples of spinal cord stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 4:
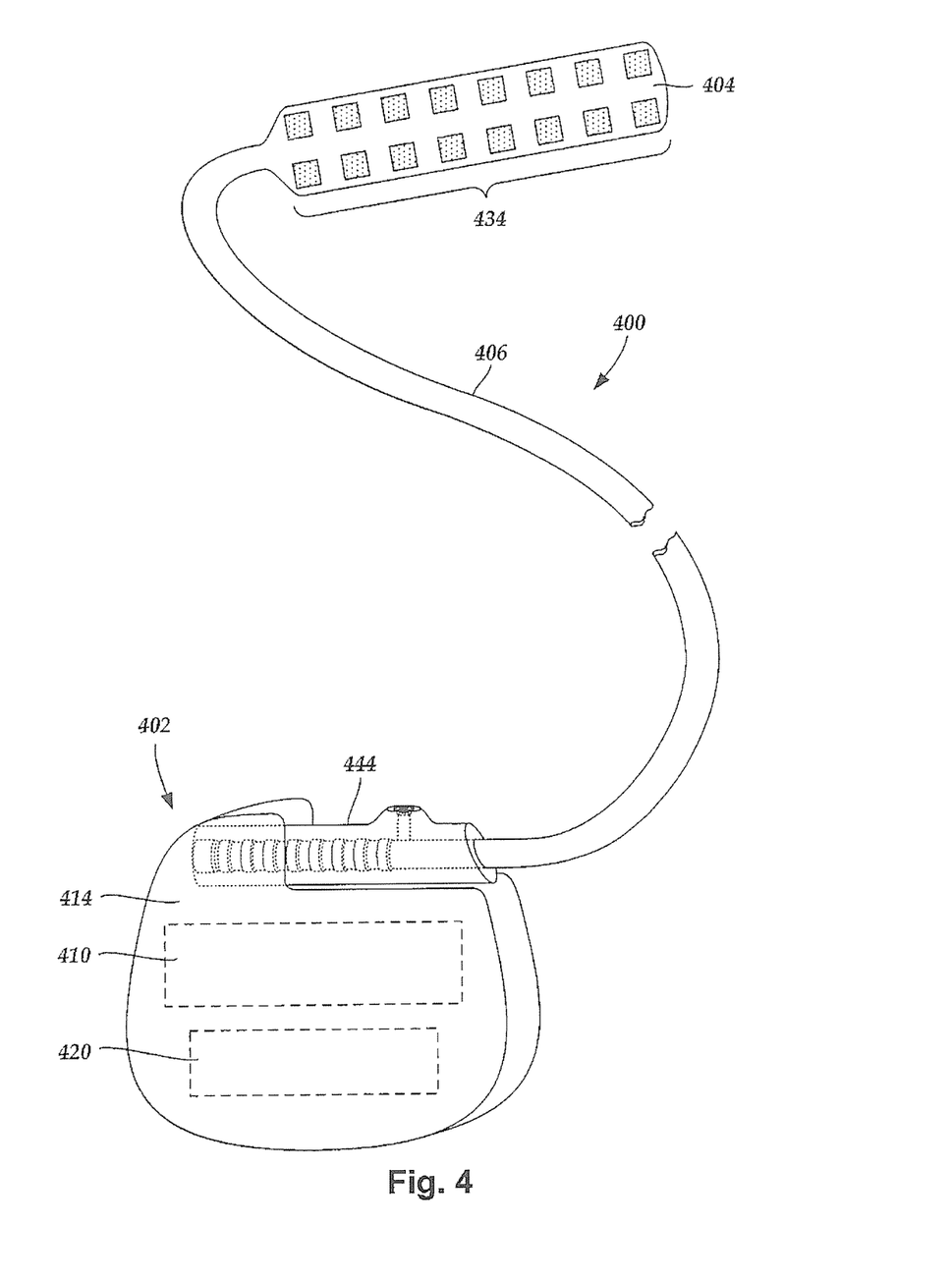
FIG. 4 is a schematic view of one embodiment of a spinal cord stimulation system, according to the invention.
Figure 5:
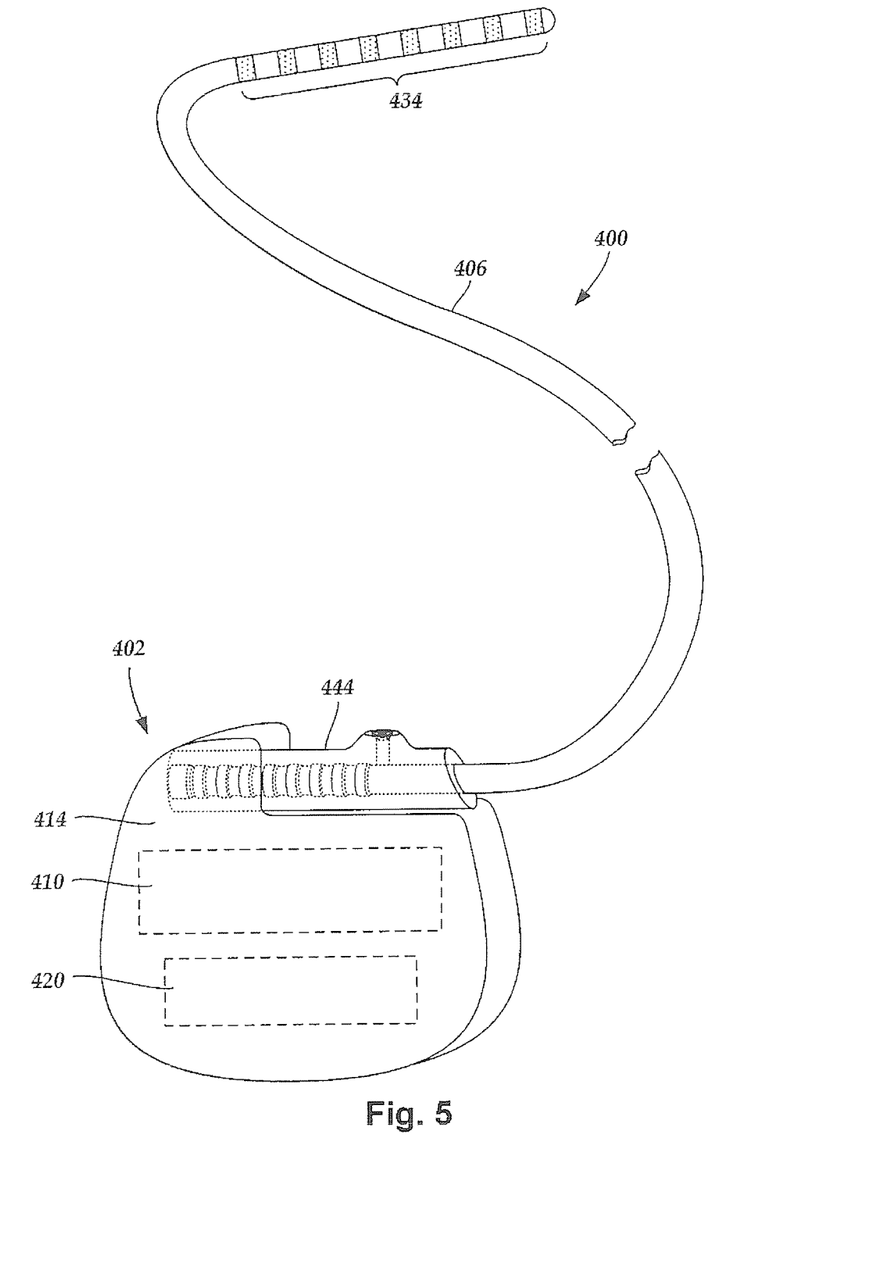
FIG. 5 is a schematic view of another embodiment of a spinal cord stimulation system, according to the invention.

FIG. 4 illustrates schematically one embodiment of a spinal cord stimulation system 400. The spinal cord stimulation system includes a control module (e.g., a stimulator or pulse generator) 402, a paddle body 404, and at least one lead body 406 coupling the control module 402 to the paddle body 404. The paddle body 404 and the one or more lead bodies 406 form a lead. The paddle body 404 typically includes an array of electrodes 434. The control module 402 typically includes an electronic subassembly 410 and an optional power source 420 disposed in a sealed housing 414. The control module 402 typically includes a connector 444 (FIGS. 5 and 6A, see also 622 and 650 of FIG. 6B) into which the proximal end of the one or more lead bodies 406 can be plugged to make an electrical connection via conductive contacts on the control module 402 and terminals (e.g., 610 in FIG. 6A and 636 of FIG. 6B) on each of the one or more lead bodies 406. It will be understood that the spinal cord stimulation system can include more, fewer, or different components and can have a variety of different configurations including those configurations disclosed in the spinal cord stimulation system references cited herein. For example, instead of a paddle body 404, the electrodes 434 can be disposed in an array at or near the distal end of the lead body 406 forming a percutaneous lead, as illustrated in FIG. 5. A percutaneous lead may be isodiametric along the length of the lead. In addition, one or more lead extensions 612 (see FIG. 6B) can be disposed between the one or more lead bodies 406 and the control module 402 to extend the distance between the one or more lead bodies 406 and the control module 402 of the embodiments shown in FIGS. 4 and 5.

The spinal cord stimulation system or components of the spinal cord stimulation system, including one or more of the lead bodies 506, the paddle body 504, and the control module 402, are typically implanted into the body of a patient. In at least some embodiments, the lead is implanted into an epidural space, between the spinal cord and the vertebral column, of a patient in proximity to the segment of the spinal cord where at least one motor nerve or at least one sensory nerve of the body portion affected by Parkinsonism attaches to the spinal cord. In at least some embodiments, the lead is in proximity to the one or more nerves of interest when the one or more nerves of interest are near enough to be contacted with stimulation pulses equal to or above a minimum therapeutic stimulation level. The minimum distance needed to ensure that the one or more nerves of interest are contacted with stimulation pulses equal to or above the minimum therapeutic stimulation level may be affected by a variety of factors including, for example, the amplitude of the stimulation pulses, the types of tissue surrounding the one or more nerves of interest, the types of tissue surrounding the lead, the types of tissue between the one or more nerves and the lead, the distance between the lead and the one or more nerves of interest, and the like.

In at least some embodiments, implantation of the lead may involve surgery. For example, in at least some embodiments, implantation of the lead involves inserting an introducer needle, such as an epidural needle, into a patient. Once the introducer needle is inserted into the patient and positioned in a desired location (e.g., the epidural space in proximity to the attachment of one or more nerves to the spinal cord, the one or more nerves connected to an affected body portion), the lead is inserted into the introducer needle. Once the lead is fully inserted in the introducer sheath, the introducer needle is pulled out of the patient by sliding the introducer needle off a proximal end of the lead. The proximal end of the lead may then be electrically coupled to a control module and implanted in the patient, or the proximal end of the lead may be electrically connected to an external trial stimulator for trial stimulation to test the efficacy of the spinal cord stimulation system 400. In at least some embodiments, implantation of the lead may involve more invasive surgery. For example, implantation of a paddle lead may require a laminectomy. Additionally, other techniques may be needed to properly position the paddle lead in the desired location.

The electrodes 434 can be formed using any conductive, biocompatible material. Examples of suitable materials include metals, alloys, conductive polymers, conductive carbon, and the like, as well as combinations thereof. The number of electrodes 434 in the array of electrodes 434 may vary. For example, there can be two, four, six, eight, ten, twelve, fourteen, sixteen, or more electrodes 434. As will be recognized, other numbers of electrodes 434 may also be used.

The electrodes of the paddle body 404 or one or more lead bodies 406 are typically disposed in, or separated by, a non-conductive, biocompatible material including, for example, silicone, polyurethane, polyetheretherketone ("PEEK"), epoxy, and the like or combinations thereof. The paddle body 404 and one or more lead bodies 406 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 406. The non-conductive, biocompatible material of the paddle body 404 and the one or more lead bodies 406 may be the same or different. The paddle body 404 and the one or more lead bodies 406 may be a unitary structure or can be formed as two separate structures that are permanently or detachably coupled together.

Terminals (e.g., 610 in FIG. 6A and 636 of FIG. 6B) are typically disposed at the proximal end of the one or more lead bodies 406 for connection to corresponding conductive contacts (e.g., 614 in FIG. 6A and 640 of FIG. 6B) in connectors (e.g., 444 in FIGS. 4-6A and 622 and 650 of FIG. 6B) disposed on, for example, the control module 402 (or to other devices, such as conductive contacts on a lead extension, an operating room cable, or an adaptor). Conductive wires ("conductors") (not shown) extend from the terminals (e.g., 610 in FIG. 6A and 636 of FIG. 6B) to the electrodes 434. Typically, one or more electrodes 434 are electrically coupled to a terminal (e.g., 610 in FIG. 6A and 636 of FIG. 6B). In some embodiments, each terminal (e.g., 610 in FIG. 6A and 636 of FIG. 6B) is only connected to one electrode 434. The conductors may be embedded in the non-conductive material of the lead or can be disposed in one or more lumens (not shown) extending along the lead. In some embodiments, there is an individual lumen for each conductor. In other embodiments, two or more conductors may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 404. In at least one embodiment, the one or more lumens may be flushed continually, or on a regular basis, with saline, epidural fluid, or the like. In at least some embodiments, the one or more lumens can be permanently or removably sealable at the distal end.

Figure 6A:
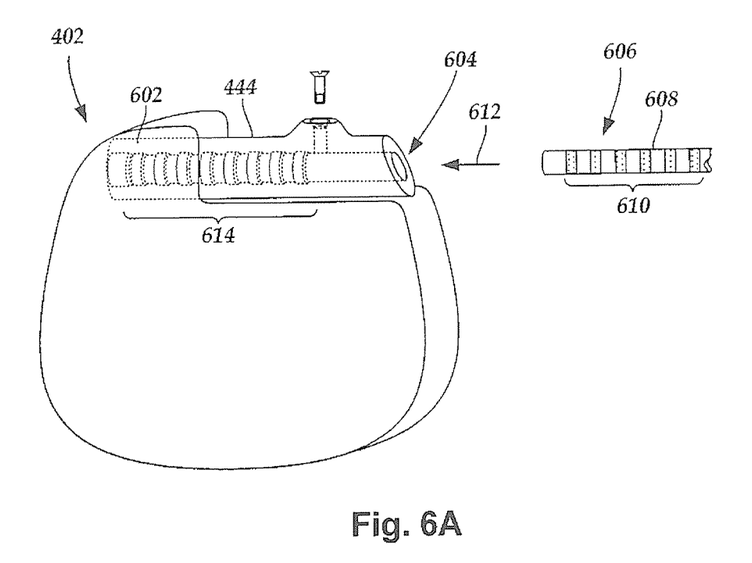
FIG. 6A is a schematic view of one embodiment of a proximal portion of a lead and a control module of a spinal cord stimulation system, according to the invention.

In at least some embodiments, leads are coupled to connectors disposed on control modules. In FIG. 6A, a lead 608 is shown configured and arranged for insertion to the control module 402. The connector 444 includes a connector housing 602. The connector housing 602 defines at least one port 604 into which a proximal end 606 of a lead 608 with terminals 610 can be inserted, as shown by directional arrow 612. The connector housing 602 also includes a plurality of conductive contacts 614 for each port 604. When the lead 608 is inserted into the port 604, the conductive contacts 614 can be aligned with the terminals 610 on the lead 608 to electrically couple the control module 402 to the electrodes (434 of FIG. 4) disposed at a distal end of the lead 608. Examples of connectors in control modules are found in, for example, U.S. Pat. No. 7,244,150 and U.S. patent application Ser. No. 11/532,844, which are incorporated by reference.

Figure 6B:
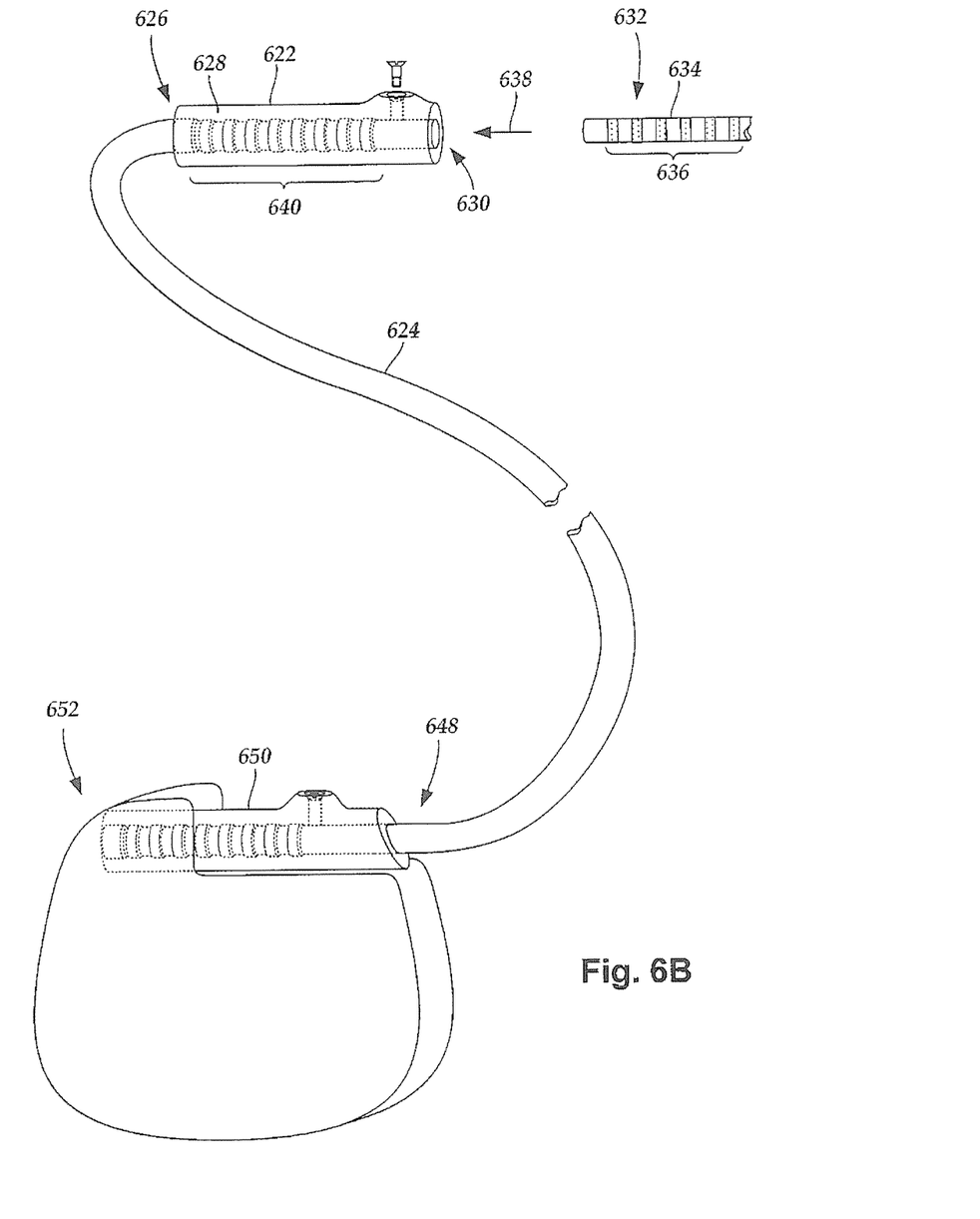
FIG. 6B is a schematic view of one embodiment of a proximal portion of a lead and a lead extension of a spinal cord stimulation system, according to the invention.

In FIG. 6B, a connector 622 is disposed on a lead extension 624. The connector 622 is shown disposed at a distal end 626 of the lead extension 624. The connector 622 includes a connector housing 628. The connector housing 628 defines at least one port 630 into which a proximal end 632 of a lead 634 with terminals 636 can be inserted, as shown by directional arrow 638. The connector housing 628 also includes a plurality of conductive contacts 640. When the lead 634 is inserted into the port 630, the conductive contacts 640 disposed in the connector housing 628 can be aligned with the terminals 636 on the lead 634 to electrically couple the lead extension 624 to the electrodes (434 of FIG. 4) disposed at a distal end (not shown) of the lead 634.

In at least some embodiments, the proximal end of a lead extension is similarly configured and arranged as a proximal end of a lead. The lead extension 624 may include a plurality of conductors (not shown) that electrically couple the conductive contacts 640 to a proximal end 648 of the lead extension 624 that is opposite to the distal end 626. In at least some embodiments, the conductive wires disposed in the lead extension 624 can be electrically coupled to a plurality of terminals (not shown) disposed on the proximal end 648 of the lead extension 624. In at least some embodiments, the proximal end 648 of the lead extension 624 is configured and arranged for insertion into a connector disposed in another lead extension. In other embodiments, the proximal end 648 of the lead extension 624 is configured and arranged for insertion into a connector disposed in a control module. As an example, in FIG. 6B the proximal end 648 of the lead extension 424 is inserted into a connector 650 disposed in a control module 652.

Figure 7:
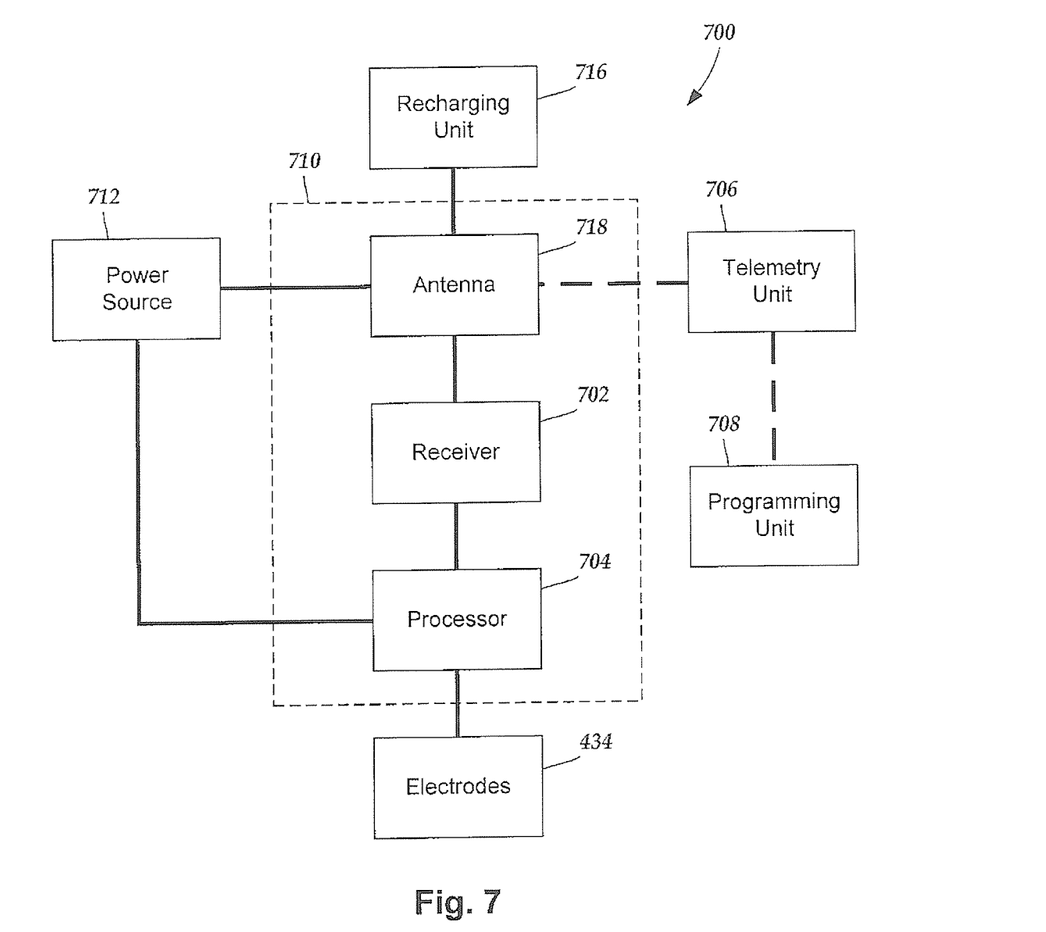
FIG. 7 is a schematic overview of one embodiment of components of a spinal cord stimulation system, including an electronic subassembly disposed within a control module, according to the invention.

FIG. 7 is a schematic overview of one embodiment of components of a spinal cord stimulation system 700 including an electronic subassembly 710 disposed within a control module. It will be understood that the spinal cord stimulation system can include more, fewer, or different components and can have a variety of different configurations including those configurations disclosed in the stimulator references cited herein.

Some of the components (for example, power source 712, antenna 718, receiver 702, and processor 704) of the spinal cord stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 434 on the paddle or lead body to stimulate nerve fibers, muscle fibers, or other body tissues near the spinal cord stimulation system. A processor 704 is generally included to control the timing and electrical characteristics of the spinal cord stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the spinal cord stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the spinal cord stimulation system. For example, the signals may be used to modify the pulses of the spinal cord stimulation system such as modifying one or more of pulse duration, pulse frequency, pulse waveform, and pulse strength. The signals may also direct the spinal cord stimulation system 700 to cease operation, to start operation, to start charging the battery, or to stop charging the battery. In other embodiments, the spinal cord stimulation system 700 does not include an antenna 718 or receiver 702 and the processor 704 operates as programmed.

Optionally, the spinal cord stimulation system 700 may include a transmitter (not shown) coupled to the processor 704 and the antenna 718 for transmitting signals back to the telemetry unit 706 or another unit capable of receiving the signals. For example, the spinal cord stimulation system 700 may transmit signals indicating whether the spinal cord stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The stimulating current that is output by an implanted spinal cord stimulation system is not constant, but is delivered in a regular cycle. Consequently, there are a number of parameters that characterize the current that is output by the implanted spinal cord stimulation system 700. As noted above, the effect of the stimulation can be controlled by adjusting these parameters of the stimulation current. For example, the size, intensity and character of the parasthesia created (or the location or amount of relief) can be controlled by adjusting the amplitude, frequency, pulse width, duty cycle, ramp up time, ramp down time, and other parameters of the stimulation current. One or more of the abovementioned parameters can be adjusted to tailor the stimulation to the needs of a particular patient.

In at least some embodiments, a range of stimulation frequencies may be used that includes one or more frequencies of no less than 2 Hertz. In at least some embodiments, a range of stimulation frequencies may be used that includes one or more frequencies of no more than 200 Hertz. In at least some embodiments, a range of stimulation frequencies may be used that includes one or more frequencies of no more than 150 Hertz. In at least some embodiments, a range of pulse widths for stimulation currents may be used that includes pulse widths of at least 50 microseconds. In at least some embodiments, a range of pulse widths for stimulation currents may be used that includes pulse widths of no more than 1500 microseconds.

The abovementioned parameters can be adjusted over various ranges to determine the best result for a particular patient. Stimulation adjustment may also be achieved by manually moving one or more electrodes relative to the stimulation site. Different sets or programs of stimulation current parameters may be applied at different times or to different nerves to adjust the relief from Parkinsonism afforded to a patient.

In at least some embodiments, spinal cord stimulation systems include multiple pre-programmed settings. In at least some embodiments, the spinal cord stimulation system may cycle through two more different settings either automatically or manually. In at least some embodiments, at least one of the settings corresponds to providing patient relief tailored to a specific patient activity (e.g., lying horizontally, standing, sitting, and the like). In at least some embodiments, a patient may be able to select a desired preprogrammed setting at will. In at least some embodiments, the patient may be able to adjust other functions as well, such as the intensity of the current setting.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for treating essential tremor or Parkinsonism using spinal cord stimulation, the method comprising:
   implanting a lead in an epidural space of a spinal cord of a patient at a position adjacent to one or more segments of the spinal cord, wherein each of the one or more segments are lumbar or sacral segments or thoracic segments in a range from T7 to T12, the lead comprising a plurality of electrodes disposed on a distal end of the lead and electrically coupled to at least one contact terminal disposed on a proximal end of the lead; and
   providing electrical signals from a control module coupled to the lead to stimulate the one or more segments of the spinal cord of the patient adjacent to which the lead is implanted using at least one of the electrodes, wherein the electrical signals reduce, alleviate, or eliminate at least one adverse effect of essential tremor or Parkinsonism.

2. The method of claim 1, wherein implanting the lead comprises implanting the lead such that at least one of the electrodes is in proximity to a segment of the spinal cord to which at least one nerve attaches, the at least one nerve also attaching to at least one skeletal muscle at a portion of the patient's body that is adversely affected by essential tremor or Parkinsonism.

3. The method of claim 1, wherein implanting the lead comprises implanting the lead near a portion of the spinal cord with nerve roots extending to a lower extremity.

4. The method of claim 1, wherein the electrical signals reduce, alleviate, or eliminate tremors associated with essential tremor or bradykinesia, shuffling gate, stooping posture, or tremors associated with Parkinsonism.

5. The method of claim 3, wherein the electrical signals reduce, alleviate, or eliminate pain associated with essential tremor or Parkinsonism.

6. The method of claim 3, wherein implanting the lead comprises implanting at least one of a percutaneous lead, a paddle lead, or a cuff lead.

7. The method of claim 3, further comprising adjusting stimulation parameters of the electrical signals to reduce, alleviate, or eliminate the at least one adverse effect of essential tremor or Parkinsonism.

8. A method for treating restless leg syndrome using spinal cord stimulation, the method comprising:

implanting a lead in an epidural space of a spinal cord of a patient at a position adjacent to one or more segments of the spinal cord, wherein each of the one or more segments are lumbar or sacral segments or thoracic segments in a range from T7 to T12, the lead comprising a plurality of electrodes disposed on a distal end of the lead and electrically coupled to at least one contact terminal disposed on a proximal end of the lead; and providing electrical signals from a control module coupled to the lead to stimulate the one or more segments of the spinal cord of the patient adjacent to which the lead is implanted using at least one of the electrodes, wherein the electrical signals reduce, alleviate, or eliminate at least one adverse effect of restless leg syndrome.

9. The method of claim 8, wherein implanting the lead comprises implanting the lead such that at least one of the electrodes is in proximity to a segment of the spinal cord to which at least one nerve attaches, the at least one nerve also attaching to at least one skeletal muscle at a portion of the patient's body that is adversely affected by restless leg syndrome.

10. The method of claim 8, wherein implanting the lead comprises implanting the lead near a portion of the spinal cord with nerve roots extending to a lower extremity.

11. The method of claim 8, wherein the electrical signals reduce, alleviate, or eliminate unpleasant sensations associated with restless leg syndrome.

12. The method of claim 8, wherein the electrical signals reduce, alleviate, or eliminate pain associated with restless leg syndrome.

13. The method of claim 8, wherein implanting the lead comprises implanting at least one of a percutaneous lead, a paddle lead, or a cuff lead.

14. The method of claim 8, further comprising adjusting stimulation parameters of the electrical signals to reduce, alleviate, or eliminate the at least one adverse effect of restless leg syndrome.

* * * * *